United States Patent [19]

Steele et al.

[11] Patent Number: 4,940,944

[45] Date of Patent: Jul. 10, 1990

[54] CATHODIC PROTECTION ANALYZER IN WHICH THE FUNDAMENTAL AND ODD HARMONICS OF A POWER LINE FREQUENCY ARE REMOVED

[75] Inventors: David S. Steele, Wyoming; Randolph K. Armstrong, Cincinnati; David E. Snider, Pleasant Plain, all of Ohio

[73] Assignee: Westinghouse Electric Corp., Pittsburgh, Pa.

[21] Appl. No.: 311,506

[22] Filed: Feb. 16, 1989

[51] Int. Cl.$^5$ .............................................. G01N 27/42
[52] U.S. Cl. ...................................... 324/425; 324/724
[58] Field of Search ............. 324/425, 65 CR; 307/95; 204/196

[56] References Cited

U.S. PATENT DOCUMENTS

| | | | |
|---|---|---|---|
| 2,803,797 | 8/1957 | Cowles | 324/425 |
| 3,893,026 | 7/1975 | Glazkov et al. | |
| 4,219,807 | 8/1980 | Speck et al. | 307/95 |
| 4,331,882 | 5/1982 | Hingorani | |
| 4,356,444 | 10/1982 | Saenz, Jr. | |
| 4,437,065 | 3/1984 | Woudstra | |
| 4,496,900 | 1/1985 | Distefano et al. | 324/71.1 |
| 4,591,792 | 5/1986 | Birchmeier et al. | |
| 4,644,285 | 2/1987 | Britton | |
| 4,658,365 | 4/1987 | Syrett et al. | |
| 4,664,764 | 5/1987 | Zofan | |
| 4,725,778 | 2/1988 | Brown | |
| 4,736,432 | 4/1988 | Cantrell | 455/113 |
| 4,806,850 | 2/1989 | Saumade et al. | 324/65 C R |

OTHER PUBLICATIONS

N. G. Thompson, G. T. Ruck, K. J. Walcott and G. H. Koch, "Effectiveness of Cathodic Protection—Phase IV", Mar. 1987, Gas Research Institute Final Report GRI 87/0020.
Gas Research Institute Technology Profile, "Waveform Analyzer Monitors Cathodic Protection", Jan. 1988.
McKubre, M. C. H. and Syrett, B. C., "Harmonic Spectroscopy for the Determination of Corrosion Rates in Cathodically Protected Systems", ASTM Special Publication 908, 1984, pp. 433–458.
Bertocci, U., "AC Induced Corrosion, The Effect of an Alternating Voltage on Electrodes Under Charge–Transfer Control", in Corrosion, NACE, v. 35, No. 5, May 1979, pp. 211–215.

*Primary Examiner*—Gerard R. Strecker
*Assistant Examiner*—Maura K. Regan
*Attorney, Agent, or Firm*—R. P. Lenart

[57] ABSTRACT

An instrument for measuring cathodic protection voltage levels receives a signal representative of an externally applied, full-wave rectified power line frequency cathodic protection potential, which is subject to electrical interference. The fundamental power line frequency component and odd harmonics of that fundamental component are removed to produce a filtered signal. Selected parameters of the filtered signal are measured to provide an indication of the adequacy of the cathodic protection potential.

8 Claims, 2 Drawing Sheets

4,940,944

CATHODIC PROTECTION ANALYZER IN WHICH THE FUNDAMENTAL AND ODD HARMONICS OF A POWER LINE FREQUENCY ARE REMOVED

BACKGROUND OF THE INVENTION

This invention relates to instruments for measuring cathodic protection voltage levels and to the method used by such instruments to measure the voltage.

The oil and gas transmission industry uses cathodic protection on buried metal pipelines to minimize the amount of pipeline corrosion. Transmission pipe lines use a system which supplies a current through the pipe and a ground bed, causing the pipe to appear as a cathode of a chemical cell. The chemical action of the cathode is to take on particles. If the pipe were to be anodic rather than cathodic, the pipe would corrode and eventually cause a failure. Typical power supplies used to induce the cathodic protection voltage include a full-wave rectifier which outputs a signal derived from a commercial power line, generally 60 Hz AC. The resulting 120 Hz pulsating signal is applied between the pipeline and an associated ground bed in an attempt to maintain a suitable DC cathodic protection level. The applied voltage may or may not be filtered.

Test points are periodically provided along the pipeline to permit verification of the required cathodic voltage protection levels. Established standards provide that the level of cathodic protection is acceptable if it meets any one of at least five criteria. One of these criterias states that the pipeline should have a −0.85 V (or more negative) potential with reference to a copper-copper sulfate (Cu-CuSo$_4$) probe. Such measurements are typically performed by using a high impedance average reading volt meter. Occasionally, inaccurate readings may be obtained because power line interference mixes with the desired signal measurement and the signal parameter being measured is not accurately measured due to noise induced on the ground path. Furthermore, the cathodic protection wave-form will often rise above the pipeline protection criteria for short periods during this 120 Hz wave-form. This condition, which is not detected using conventional average reading volt meters, may contribute to particle corrosion and should be detected.

This invention seeks to provide more accurate measurements of the cathodic protection voltage levels and to process the cathodic protection voltage level signals so that additional information, such as peak voltage or percentage of time that the voltage is above a threshold, may be obtained therefrom.

SUMMARY OF THE INVENTION

In active cathodic protection systems which utilize a full-wave rectifier receiving power from a 60 Hz commercial source, the cathodic protection voltage signal of interest includes a DC component, a 120 Hz component, and harmonics of the 120 Hz component. Unwanted power line interference is concentrated at the power source fundamental frequency (usually 60 Hz) and odd order harmonics thereof. This invention eliminates fundamental power line frequency noise component and odd order harmonics generated by power line interference to provide an accurate measurement of the DC and 120 Hz cathodic protection voltages.

An instrument for measuring cathodic protection voltage constructed in accordance with the present invention receives a signal representative of an externally applied, full-wave rectified power line frequency cathodic protection potential which is subject to electrical interference. The fundamental power line frequency component and odd harmonics thereof are removed from the signal, thereby producing a filtered signal. Selected parameters of the filtered signal are then measured to produce an indication of the adequacy of the cathodic protection potential.

Rapid voltage variations in the cathodic protection wave-form, which occur at 120 Hz for systems supplied by 60 Hz power sources, are not detected by typical average reading volt meters. Since these variations may contribute to the corrosion process if they exceed certain voltage thresholds, valuable quantitative information concerning the adequacy of cathodic protection levels may be obtained by measuring various parameters associated with these rapid voltage variations.

BRIEF DESCRIPTION OF THE DRAWINGS

The invention will become more readily apparent from the following description of the preferred embodiment thereof, shown by way of example only, in the accompanying drawings wherein.

DESCRIPTION OF THE PREFERRED EMBODIMENT

Figure 1:
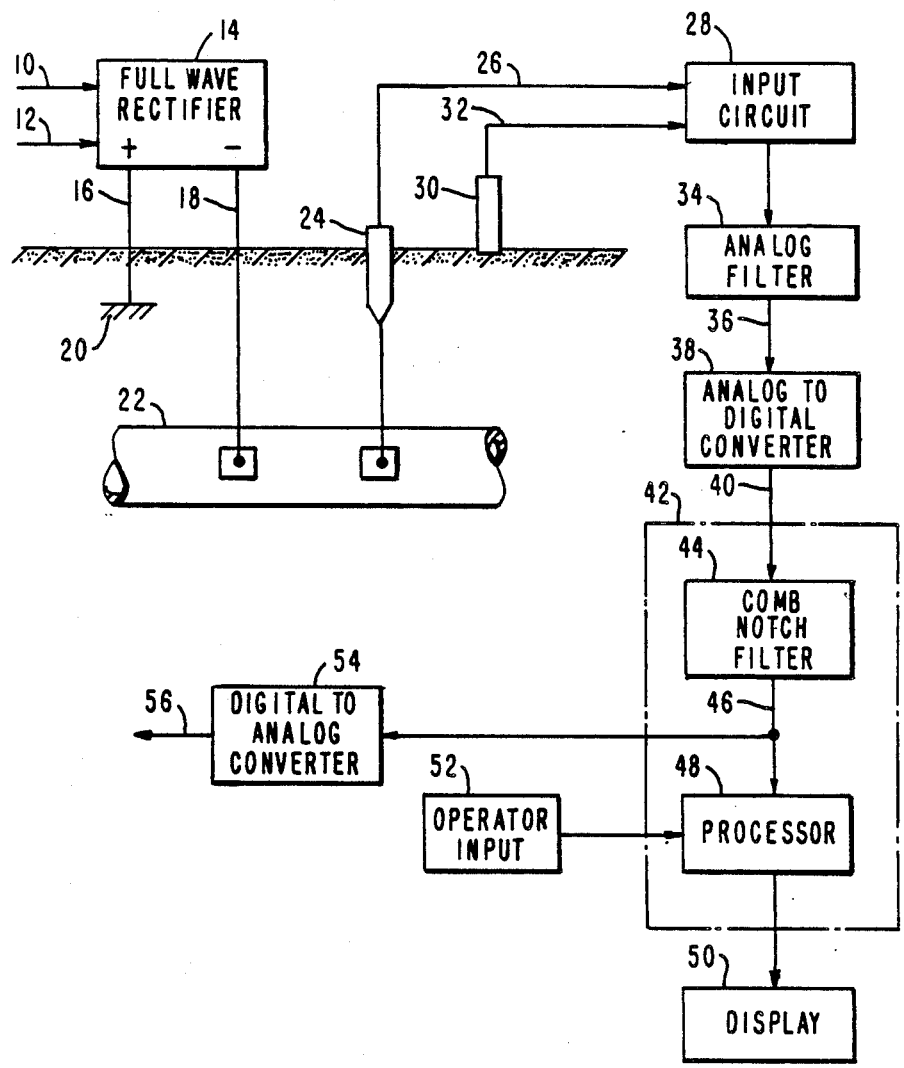
FIG. 1 is a block diagram of a cathodic protection analyzer constructed in accordance with one embodiment of the present invention.

Referring to the drawings, FIG. 1 is a block diagram of a cathodic protection analyzer constructed in accordance with one embodiment of the present invention. In the type of active cathodic protection systems to which this invention applies, commercial line power, at a nominal 60 Hz frequency in this example, is supplied on lines 10 and 12. A full-wave rectifier 14 converts this input to a 120 Hz pulsating DC output on lines 16 and 18. Line 16 is connected to an anodic ground bed 20 constructed in accordance with known techniques. The negative line 18 is connected to an underground pipeline 22. A test point 24, which may be one of many periodically spaced along the pipeline, is provided for connection via line 26 to an input circuit 28 (which may be an amplifier or attenuator) in the cathodic protection analyzer. A standard reference electrode 30 which may be a copper-copper sulfate half cell, is placed in contact with the ground in accordance with known techniques and is connected to the cathodic protection analyzer via line 32. In this manner, the input circuit receives a first signal representative of an externally applied, full-wave rectified power line frequency cathodic protection potential which is subject to electrical interference.

A 60 Hz analog filter 34 is used to remove the majority of the fundamental power line frequency noise component from the cathodic protection signal which is produced by the input circuit. The resulting filtered analog signal on line 36 is converted to digital form by an analog to digital converter 38. This results in a first digital signal on line 40 which is fed to a microcomputer 42. The microcomputer includes a comb notch filter which removes the remainder of the fundamental power line frequency component and, add harmonics thereof from the first digital signal thereby producing a filtered digital signal on line 46. This filtered digital signal is fed to the processor 48 of the microcomputer which measures a selected parameter of the filtered digital signal to produce an indication of the adequacy of the cathodic protection potential. This indication is then delivered to a display device 50. Selection of the particular parameter of interest can be made by an operator using an input device 52. A digital to analog converter 54 receives the filtered digital signal on line 46 to produce an analog signal on line 56 that is representative of the original received cathodic protection signal with the fundamental power line frequency component and odd harmonics thereof removed.

Figure 2:
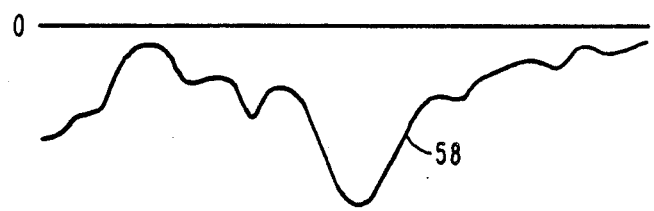
FIG. 2 is a wave-form illustrative of the type of input signal received by the analyzer of FIG. 1.
Figure 3:
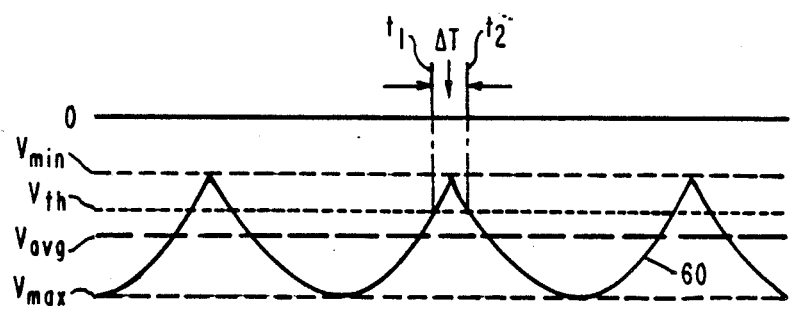
FIG. 3 is a wave-form of the filtered output signal of the analyzer of FIG. 1.

FIG. 2 is a wave-form which is illustrative of the type of cathodic protection voltage signal 58 that may be received on lines 26 and 32 of FIG. 1. It is apparent that this input signal has been subjected to significant electrical interference. FIG. 3 is a wave-form that is illustrative of the type of output wave-form 60 which would appear on line 56 of FIG. 1. Wave-form 60 can be used to illustrate some of the parameters which may be measured by processor 48 and transmitted to the display. These parameters include the minimum cathodic protection voltage $V_{min}$, the average cathodic protection voltage $V_{avg}$ and the maximum cathodic protection voltage $V_{max}$. Because the cathodic protection voltage is defined as being negative with respect to a reference electrode, for the purposes of this description of the preferred embodiment of the invention, the minimum cathodic protection voltage $V_{min}$ is the least negative voltage level and the maximum cathodic protection voltage $V_{max}$ is the most negative voltage level as illustrated in FIG. 3. The time per cycle $\Delta T$ in which the cathodic protection voltage level exceeded some preselected threshold level $V_{th}$ may also be displayed. Another parameter of interest which may be calculated is the integral of the cathodic protection voltage level over the time period between $t_1$ and $t_2$ in which it exceeded the selected protection threshold level. The integrated value combines the voltage and time when the protection exceeds the threshold and may indicate the relative susceptibility of the pipe to instantaneous corrosion.

Since the cathodic protection analyzer of this invention is capable of measuring and displaying the least negative wave-form value, the most negative wave-form value, the average wave-form value, the time that the wave-form exceeds a selectable voltage threshold, and the integral of the voltage over the time that the wave-form exceeded that threshold, it is clear that the present invention provides significantly more information than that provided by conventional measurement techniques. The additional parameters provided by this invention yield quantitative information about the quality of the cathodic protection level.

Although the present invention has been described in terms of what is at present believed to be its preferred embodiment, it will be apparent to those skilled in the art that various changes may be made without departing from the scope of the invention. For example, the power line fundamental frequency analog filter 34 was included in the preferred embodiment because of a limited dynamic range of the analog to digital converter 38. The analog filter could be eliminated by increasing the dynamic range of the analog to digital converter, such as by adding more bits of resolution. Alternative filtering schemes also fall within the scope of this invention. For example, the comb notch filter 44 could be replaced by a bank of analog or digital filters cascaded in series. Yet another approach would be the performance of the filter function in the frequency domain. In that instance, the signal would be converted to the frequency domain after sampling by using a Fourier Transform. After that, the signal would be represented as a function of energy versus frequency, rather than amplitude versus time. By picking out the frequencies corresponding to the rectified power line frequency signal, the same parameters that are measured in the time domain can be derived. It is therefore intended that the appended claims cover such changes.

What is claimed is:

1. A method of measuring cathodic protection voltage, said method comprising the steps of:
   receiving a first signal representative of an externally applied, full wave rectified power line frequency cathodic protection potential, said first signal being subject to electrical interference;
   removing a fundamental power line frequency component and odd harmonics of said power line frequency component from said first signal, thereby producing a filtered signal; and
   measuring the integral of the filtered signal over a period in which said filtered signal exceeds a predetermined magnitude, to produce an indication of the adequacy of the cathodic protection potential.

2. The method of measuring cathodic protection voltage as recited in the claim 1, wherein said fundamental component has a frequency of 60 Hz.

3. A method of measuring cathodic protection voltage, said method comprising the steps of:
   receiving a first signal representative of an externally applied, full wave rectified power line frequency cathodic protection potential, said first signal being subject to electrical interference;
   using an analog filter to remove a first portion of a fundamental power line frequency component from said first signal, thereby producing a filtered analog signal;
   digitizing said filtered analog signal, thereby producing a first digital signal;
   using a digital filter to remove a remaining portion of said fundamental power line frequency component and odd harmonics of said fundamental power line frequency component from said first digital signal, thereby producing a filtered digital signal; and
   measuring the integral of the filtered digital signal over a period in which said filtered digital signal exceeds a predetermined magnitude, to produce an indication of the adequacy of the cathodic protection potential.

4. The method of measuring cathodic protection voltage as recited in claim 3, wherein said fundamental component has a frequency of 60 Hz.

5. An instrument for measuring cathodic protection voltage comprising:
   means for receiving a first signal representative of an externally applied, full wave rectified power line frequency cathodic protection potential, said first signal being subject to electrical interference;
   means for removing a fundamental power line frequency component and odd harmonics of said fundamental power line frequency component from said first signal, thereby producing a filtered signal; and
   means for measuring the integral of the filtered signal over a period in which said filtered signal exceeds a predetermined magnitude, to produce an indication of the adequacy of the cathodic protection potential.

6. An instrument for measuring cathodic protection voltage as recited in claim 5, wherein said means for removing said odd harmonics of the fundamental power line frequency component comprises a comb notch filter.

7. An instrument for measuring cathodic protection voltage comprising:
   means for receiving a first signal representative of an externally applied, full wave rectified power line frequency cathodic protection potential, said first signal being subject to electrical interference;
   an analog filter for removing a first portion of a fundamental power line frequency component from said first signal, thereby producing a filtered analog signal;
   means for digitizing said analog filtered signal, thereby producing a first digital signal;
   a digital filter for removing a remaining portion of said fundamental power line frequency component and odd harmonics of said fundamental power line frequency component from said first digital signal, thereby producing a filtered digital signal; and
   means for measuring the integral of the filtered digital signal over a period in which said filtered digital signal exceeds a predetermined magnitude, to produce an indication of the adequacy of the cathodic protection potential.

8. An instrument for measuring cathodic protection voltage as recited in claim 7, wherein said means for removing said odd harmonics of said fundamental power line frequency component comprises a comb notch filter.

* * * * *